(12) United States Patent
Hofmann et al.

(10) Patent No.: US 8,782,206 B2
(45) Date of Patent: Jul. 15, 2014

(54) LOAD-BALANCED ALLOCATION OF MEDICAL TASK FLOWS TO SERVERS OF A SERVER FARM

(75) Inventors: Ralf Hofmann, Puschendorf (DE); Andreas Schülke, Herzogenaurach (DE); Andreas Siwick, Erlangen (DE); Hans-Martin Von Stockhausen, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 664 days.

(21) Appl. No.: 12/461,848

(22) Filed: Aug. 26, 2009

(65) Prior Publication Data

US 2010/0057828 A1    Mar. 4, 2010

(30) Foreign Application Priority Data

Aug. 27, 2008 (DE) .......................... 10 2008 040 009

(51) Int. Cl.
*G06F 15/173* (2006.01)

(52) U.S. Cl.
USPC ........... 709/224; 709/202; 709/226; 709/227; 709/228; 709/201; 718/100; 718/105

(58) Field of Classification Search
USPC ....................................................... 709/202
See application file for complete search history.

(56) References Cited

U.S. PATENT DOCUMENTS

| | | | |
|---|---|---|---|
| 6,327,622 B1 * | 12/2001 | Jindal et al. | 709/228 |
| 6,963,917 B1 * | 11/2005 | Callis et al. | 709/227 |
| 7,127,716 B2 | 10/2006 | Casati | |
| 7,882,501 B1 * | 2/2011 | Carlson et al. | 717/167 |
| 2002/0164059 A1 * | 11/2002 | DiFilippo et al. | 382/128 |
| 2003/0014524 A1 * | 1/2003 | Tormasov | 709/226 |
| 2003/0046396 A1 * | 3/2003 | Richter et al. | 709/226 |
| 2004/0158637 A1 * | 8/2004 | Lee | 709/226 |
| 2005/0033809 A1 * | 2/2005 | McCarthy et al. | 709/205 |
| 2005/0096877 A1 * | 5/2005 | Shimazaki et al. | 702/186 |
| 2005/0120095 A1 * | 6/2005 | Aman et al. | 709/219 |
| 2006/0168334 A1 * | 7/2006 | Potti et al. | 709/239 |
| 2007/0143460 A1 * | 6/2007 | Ben-David et al. | 709/223 |
| 2009/0204711 A1 * | 8/2009 | Binyamin | 709/226 |
| 2010/0161714 A1 * | 6/2010 | Dongre | 709/203 |

OTHER PUBLICATIONS

Nentec 2006, Nitro-Switch, http://www.nentec.de/nitro-loadbalancing.htm, http://www.nentec.de/nitro-ha.htm.

* cited by examiner

*Primary Examiner* — Hamza Algibhah
*Assistant Examiner* — Natisha Cox
(74) *Attorney, Agent, or Firm* — Harness, Dickey & Pierce, P.L.C.

(57) ABSTRACT

A method, a system and a computer program are disclosed for the load-balanced allocation of computer-aided medical task flows on at least one application server of a server farm. In at least one embodiment, request conditions and load information are configured in a configuration phase. The request conditions are then recorded in a load balancing phase. In addition the load information is recorded via load calculation agents. A load balancing service can then calculate a target application server, which according to the load information determined meets all recorded request conditions.

17 Claims, 2 Drawing Sheets

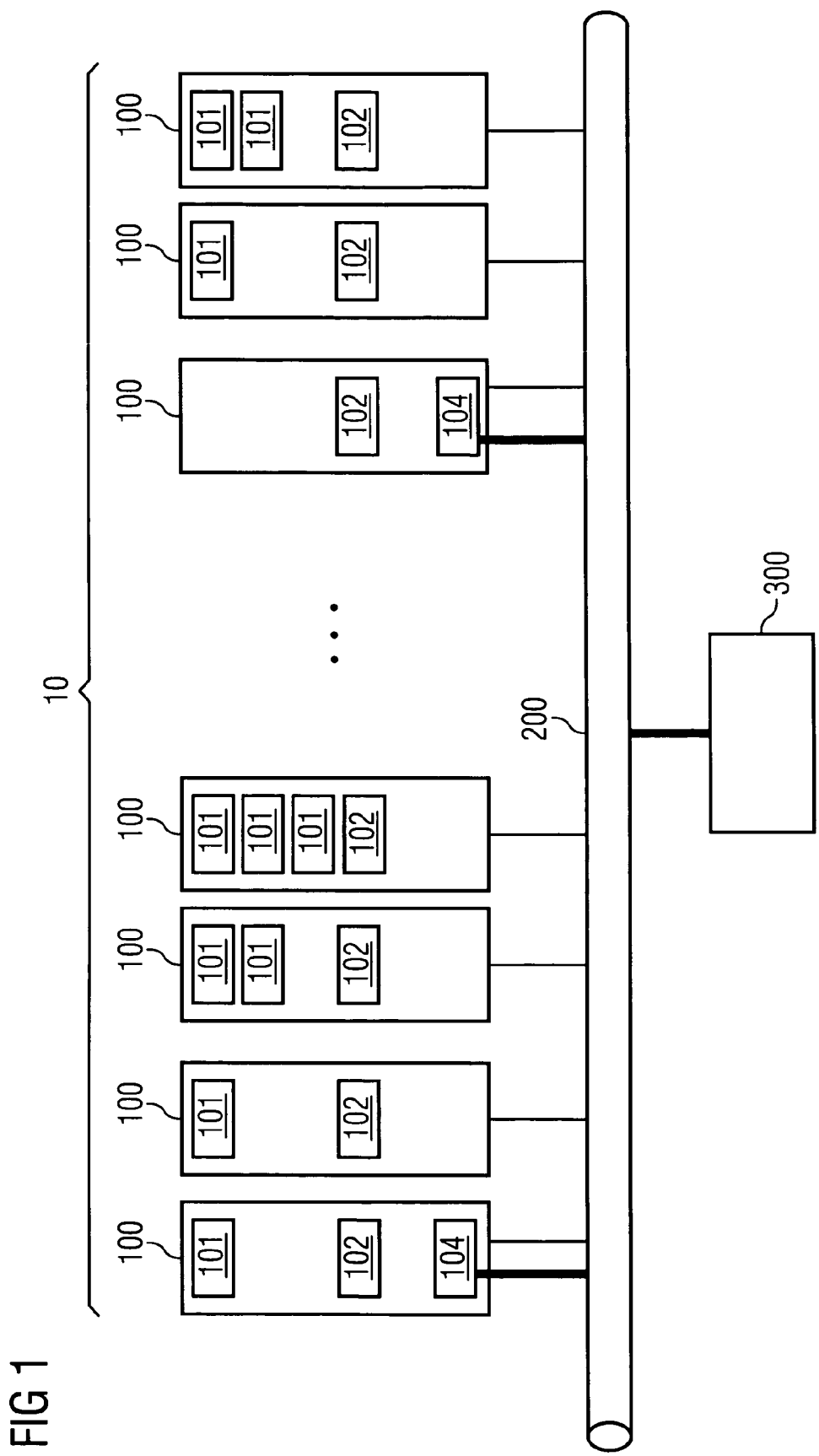

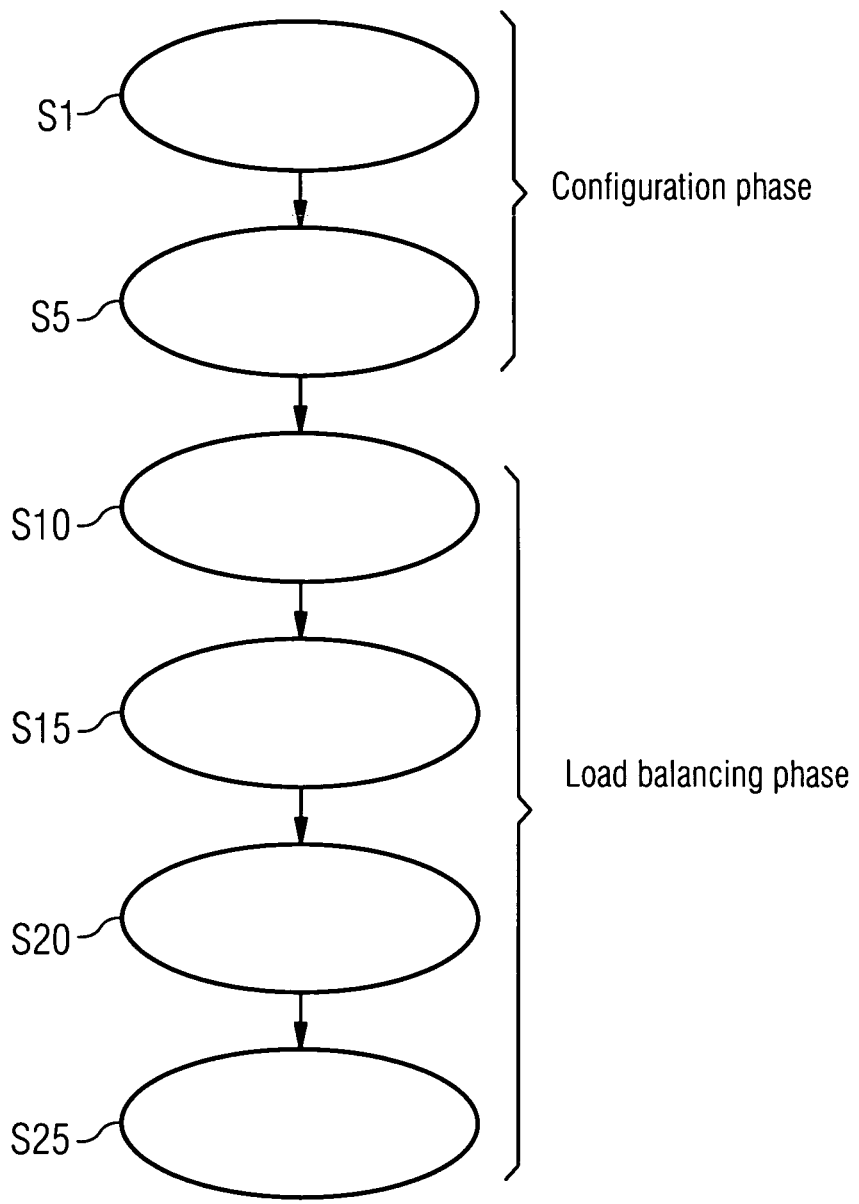

LOAD-BALANCED ALLOCATION OF MEDICAL TASK FLOWS TO SERVERS OF A SERVER FARM

PRIORITY STATEMENT

The present application hereby claims priority under 35 U.S.C. §119 on German patent application number DE 10 2008 040 009.2 filed Aug. 27, 2008, the entire contents of which are hereby incorporated herein by reference.

FIELD

At least one embodiment of the invention is in the field of medical engineering, and generally relates to load balancing for complex medical task flows within a server farm.

BACKGROUND

As a rule, day-to-day clinical activities are nowadays based on a group of servers, to which a group of clients has access. The client-server system serves to handle the processing of complex medical task flows. This might involve, for instance, modular and/or nested workflows, relating for example to an MRI examination, a laboratory investigation and the subsequent post-processing of the data. Here the investigation on the MRI scanner encompasses various sub-tasks, such as for example the generation of a suitable measurement sequence for the investigation to be performed and the adaptation of the particular measurement sequence to the MR scanner. In order to be able to carry out the clinical operations as efficiently as possible, it is important to assign the tasks to be executed to the suitable server in each case. In particular the servers must have the appropriate technical prerequisites in order to be able to perform the task at all.

A large number of methods in the field of load calculation/load balancing are known from information technology. A distinction is drawn here between two different approaches: On the one hand are software-based and hardware-based load balancing systems. One example of a software-based approach is the load balancing system from Microsoft, which is known as Microsoft Network Loadbalancing (NLB). Here, incoming data packets for processing are forwarded to all basically available server machines. A check is then performed to ascertain which server machine is best suited to the service or the particular packet concerned. This server machine is then identified, and prepared for the processing of the data packet. The data packet received is then deleted on all the other server machines. This procedure leads to relatively high levels of data traffic.

One example of a hardware-based load balancing is the "NitroSwitch" system supplied by NENTEC Netzwerktechnologie GmbH. In contrast to the Microsoft system just mentioned, here the data packet to be processed is forwarded only to that server machine on which the processing will ultimately take place.

A large number of algorithms are furthermore known from information technology, according to which load balancing can be controlled. These include, for example the so-called Weighted-Round-Robin-Method, the Weighted-Least-Connections-Method and the Weighted-Least-Traffic-Method etc. In the case of load balancing using NitroSwitch it is possible to determine which of the predefined algorithms is to be used in the particular case.

In addition to the two previously mentioned suggestions for load balancing from the prior art in the field of information technology, a plurality of further suggestions are known. In the case of the known methods the criteria based upon which load balancing takes place are, however, generally hardware-based and prescribed, and do not match the specific characteristics of a medical engineering-related task flow.

A further known system from the prior art is disclosed in U.S. Pat. No. 7,127,716 from the company Hewlett-Packard Development, the entire contents of which is incorporated herein by reference. This method is based on latency time-based load balancing, and presupposes a complex administration system for workflows. Before execution of a particular task, the server system is first calibrated with respect to the task to be executed. The workload arising is here calculated in advance and distributed in relation to the available servers such that that the overall latency time can be minimized. For a number of reasons the method proposed here is not likely to be suitable for use in a clinical or medical engineering context, as in this case medical-specific and clinical criteria must be taken into account, in order to achieve optimum load balancing.

SUMMARY

In at least one embodiment of the invention is directed to a way by which a complex medical task flow can be better distributed between a number of servers of a server farm. It should additionally be possible to integrate different versions of applications into the load balancing, while taking account of server-specific features and task flow-specific requirements in the field of medical engineering.

A solution to this problem is described below with reference to a method of at least one embodiment of the invention. Features, advantages or alternative embodiments mentioned here are likewise included. In other words, the claims relating to the subject-matter (which are, for example, oriented toward a system or a product) can be developed with the features which are described or claimed in connection with the method, and vice versa. The corresponding functional features of the method of at least one embodiment are here embodied by way of modules related to the subject-matter, in particular by way of hardware modules of the system or of the device.

A method of at least one embodiment, for the load-balanced allocation of computer-aided medical task flows on at least one application server of a server farm, comprises:
  recording of a medical task flow with configurable request conditions
  recording of load information from available application servers of the server farm, wherein it is possible—as a rule in advance—to configure what load information is to be recorded, in that at least one program extension is installed on selected or on all application servers.
  identification of at least one target application server, at least one such application server from the server farm being designated as the target application server, which fulfills the recorded request conditions according to the recorded load information.

The terms used within the context of this application are explained in greater detail below.

The term "load-balanced allocation" refers to the allocation of task flows to individual servers or a group of servers from a server farm, wherein the current server loading within the network is to be taken into account. Configurable criteria are to be employed here which are of particular relevance in the field of medical engineering.

The task flow generally takes the form of a medical task flow, comprising a sequence of several tasks which are executed in a staggered manner and/or nested within one another. The tasks are based on different applications, which for their part can be integrated into the network in different versions.

The servers of the server farm are connected to each other via a computer network, and can be designed for specific medical engineering problems. These can for example involve a postprocessing-server, special 3D volume calculation cards or MR scanners.

The request conditions relate to the task flow, and are configurable in terms of the medical problem concerned. As a rule, the request conditions encompass a series of sub-conditions, which can be linked with each other via a number of logical operators. Highly complex feature conditions can thus be formulated which must basically be met with respect to a task flow. Both the request conditions and the task flows can preferably be grouped, so that for example a request condition can be configured for a particular group of task flows.

Load information takes the form of data relating to the particular load on the application servers of the server farm. The load information can relate to a past period, a current period and a future period. Recording of the load information is performed via so-called load calculation agents. The load calculation agents are in each case installed on an application server, and serve to bring together and record load-specific information relating to the respective servers and/or relating to the network (e.g. network connections). According to a preferred embodiment of the invention it is envisaged that it is possible to set which load information is to be recorded. It is thus possible to tailor the method for the load-balanced allocation to the application situation in a highly detailed and decisive manner.

The configurability of the different conditions should be regarded as one of the significant advantages of the inventive solution. Firstly it is possible to configure the request conditions in a decisive manner. By way of a plurality of logical operators, which are provided in order to link certain sub-conditions with each other, highly complex feature conditions can be formulated as request conditions. It is for example possible to formulate that a high performance graphics card with at least two gigabytes of free main memory space is required to be able to perform a 3D rendering for the specific medical task flow. Secondly, the load information is configurable. In other words it is possible, in every application case, to determine which load information is to be recorded and qualifies as relevant. In one case, for example, it may be relevant how much main memory is available on an application server to store complex image data records, while in a second case, this feature is of no significance, and it is rather a matter of the particular computing power of the application server in order, for example, to perform complicated post-processing operations.

According to one aspect of at least one embodiment of the present invention it is envisaged that all of the aforementioned methods steps or individual ones are to be performed automatically. In this embodiment it is thus in particular envisaged that determining of a target application server is to be effected without any user interaction. It is thus possible to perform the load balancing in a far more efficient and targeted manner and to prevent the faults which arise as a result of an inappropriate application server being manually designated for a particular task flow.

At least one embodiment of the inventive method can be arranged into two time phases: Firstly there is a configuration phase, during which the request conditions can be configured and/or during which the load information can be configured. Secondly there is a load balancing phase, in which at least one target application server is actually identified. Here reference is made to the conditions and load information defined in the configuration phase. The two time phases are fundamentally independent of one another, wherein the load balancing phase must take place after the configuration phase.

According to an example embodiment of the present invention it is envisaged that the task flow is to be automatically forwarded to the target application server identified in advance for the purposes of execution. It is thus ensured that no delay needs to be bridged after the most suitable target application server has been identified and before the task can be performed on the identified target application server. The efficiency of the entire medical task flow can thus be enhanced.

As already mentioned, the request condition can be configured according to complex criteria. As a rule these comprise a plurality of sub-conditions, which can be linked via a number of logical operators (AND, OR, negation etc.). In addition nested or cascaded request conditions can be formulated. In a preferred embodiment it is envisaged that certain minimum requirements can be formulated, which can, for example, be specified in an XML file. Furthermore preferences can be formulated, by weighting a sub-condition. The following request condition can thus be formulated for example: "Volume rendering card or high performance graphics cards, if possible volume rendering card". In the above example, as a result of the defined preference an application server equipped solely with a high performance graphics card is used only as a fallback option, and only in the event that no other application server with a volume rendering card is available. Optional features can in addition be formulated as a request condition. For example it is possible to formulate the following condition: "64-bit processor if possible: with dual cores". In this example a 64-bit processor is required for a particular task flow. For optimum parallelization of the tasks contained in the task flow, however, a dual-core processor is advantageous. This feature can be specified with the request condition as previously formulated. The flexibility of the load balancing can thereby be markedly increased.

According to one aspect of at least one embodiment of the present invention, a request condition basically comprises logical features as well as physical system parameters. Accordingly, a request condition can relate exclusively to physical system parameters, exclusively logical features or a combination of the two. Examples of system parameters here include CPU load, memory occupancy, network loading etc. The system parameters relate to physically measurable values. A logical feature could be, for example, "standby server". This feature directs a search exclusively toward such application servers as are to remain reserved for emergencies.

Complete request conditions and fallback strategies for the load-balanced allocation of task flows if the target application server identified as optimal is not available can be formulated by means of the logical linkage of the plurality of sub-conditions. The possibilities for formulating alternative strategies are very extensive. The inventive method can thus advantageously be adapted to the particular application case in a very flexible manner.

It is customarily envisaged that in each case one load calculation agent is installed on one application server of the server farm.

According to a further aspect of at least one embodiment of the invention it is envisaged that a load calculation agent in each case calculates the load on the particular application server on which it is installed. This ensures a 1:1 assignment between a load calculation agent and an application server.

Basically at least one embodiment of the inventive method should culminate in the identification of at least one target application server on which the respective task flow can be executed. It is however also possible that no target application server is available. In this case the method must be repeated at a later time, at which different load information is issued. It is likewise possible that not just one target application server is identified, but rather a group of application servers which are basically possible and available. In this case it is very helpful that an additional load result is output. The load result is generally represented in the form of a list, and quantifies a number of identified target application servers based on the extent to which they fulfill the recorded request conditions. It is for example possible that a first target application server and a second target application server meet 100% of the identified request conditions, while other application servers meet only 80% of the identified application conditions. Further target application servers are then quantified according to their degree of fulfillment. A further item of information is thus provided, which indicates the result of a matching operation between recorded, configured request conditions and recorded, configured load information. This can for example be in the form of a type of hit list.

If a group of target application servers can be identified, it is envisaged in an advantageous development of the invention for the identified target application servers to be prioritized according to criteria configurable in advance. It is thus possible to identify the target application server which provides the optimal match from the number of application servers which are basically available and suitable.

A further degree of flexibility can be achieved in that the two recording processes can basically be performed independently of each other. Overall, in relation to the task flow, the recording of the request conditions can take place independently of the recording of the load information via the load calculation agents. The two recording processes can thereby be decoupled from each other. This is however only an optional feature.

According to one aspect of at least one embodiment of the present invention, the method is computer-implemented, and can be controlled by software and/or hardware modules. In particular it is envisaged that user interactions are necessary in the configuration phase, in order to enable the user inputs to be made. By contrast, the method can be executed fully automatically in the load balancing phase without further user interaction.

A further solution to the problem, in at least one embodiment, comprises a computer program, a computer program product and a system for the load-balanced allocation of computer-aided medical task flows on at least one application server of a server farm.

The system of at least one embodiment comprises a plurality of application servers of a server farm, which exchange data with each other via a computer network. The system comprises a requirements module for the recording of request conditions of the task flows. The system additionally comprises load calculation agents, which are intended to record load information relating to the application servers concerned. The system further comprises a load balancing service, which is embodied to identify a target application server, wherein the load balancing service identifies at least one application server from the server farm as the target application server, which according to the load information recorded by the load calculation agents concerned meets the request conditions recorded by the requirements module.

The load calculation agents serve to calculate the load in respect of the application server assigned to them (including the network connections and the interfaces etc.) and are not externally visible, but function as "outstations" of the load balancing service. They host all program extensions.

The load balancing service is preferably embodied centrally, and serves to receive the recorded task flows, to instruct the load calculation agents concerned, to obtain/gather and if applicable to process the calculated load information from the load calculation agents, to identify a target application server and where applicable to display a result. The load balancing service functions, as it were, as an intermediary, accepting the identified task flow with its request conditions and requesting the load information on the available application servers. The intermediary instructs all the load calculation agents involved and collects their results. These results are then compared or matched with the recorded request conditions for the task flow concerned. The load balancing service is externally visible as an interface.

According to one aspect of at least one embodiment of the invention the requirements module is embodied as an XML file, which comprises an appropriate configuration. The configuration can be generated anew or modified, so that different request conditions can be configured.

The system further comprises an interface, on which a result of at least one embodiment of the inventive method can be represented. This interface is preferably embodied on the load balancing service and can also in addition be embodied either on one load calculation agent, on a number of selected load calculation agents or on all load calculation agents. It serves to specify and represent on an interface the target application server identified or the group of identified target application servers.

According to an example embodiment, the application servers concerned are embodied with at least one program extension. The program extension can be embodied in the form of a plug-in, which is installed on the application server. Depending on the application case it is possible to provide for no program extension, just one program extension or a number of different program extensions on an application server. The program extensions serve to enable configuration or design of the load calculation in line with the particular application case. It is thus possible to configure the load balancing on a situation-specific basis.

It is furthermore possible to embody the load balancing service with further functionality, so that the intermediary automatically assigns the task flow to the identified target application server for execution purposes. In this case no further user interaction takes place.

In an example embodiment of the present invention the system thus comprises two load calculation entities: These are firstly at least one load balancing service and secondly a plurality of load calculation agents. One load calculation agent is preferably installed on each application server. According to a first variant of an example embodiment of the invention it is envisaged that only one load balancing service is embodied. This can be installed on an application server. In a second variant of an example embodiment of the invention, in order to enhance the failsafe characteristics of the entire system, the provision of a number of load balancing services can also be envisaged. These can be installed on different application servers, and are linked with each other via a network. The load balancing service can likewise be embodied on a task flow administration system or on an entity connected via the network.

The load balancing service works in dependent mode. In the dependent mode it is envisaged that the load balancing service calculates the load for the application server or the load information depending on the request conditions it receives from the task flow administration system. As soon as a request condition is linked to a task flow, this is also taken into account in all circumstances. Otherwise, that is if no request condition is assigned to the task flow, pre-configurable rules for the load balancing service take effect.

In other words it is thus envisaged that the load balancing service accesses pre-configurable rules which enable it to design the requests to the load calculation agents in a specific manner. In other words, as a result of the request conditions it may be sensible to address load calculation agents differently. Depending on the request conditions recorded, it may for example make sense initially not to address a particular load calculation agent of a particular application server at all, because the required configuration is not ready on it (for example inadequate CPU resources), while other application servers can however basically fulfill the recorded request conditions and should thus be addressed via their load calculation agents.

A load calculation agent can be given weightings, wherein the weightings in each case indicate the relevance of the load calculation agent concerned.

After recording of the load information via the plurality of load calculation agents, these can, in a development of an example embodiment of the invention, be given weighting factors depending on the application case, and are subsequently recorded by the load balancing service. The load balancing service can then identify the target application server. Thus takes place by comparing the recorded load information with the recorded request conditions. In the case of successful matching (that is the required request conditions could be met by a particular application server according to the load calculation agent) the task flow is forwarded to the particular target application server for the purposes of execution.

The inventive embodiments of the method described above can also be embodied as a computer program product, wherein the computer is prompted to perform the inventive method described above, if the program is executed on the computer or as the case may be a processor of the computer.

An alternative solution to the problem in an at least one embodiment envisages a storage medium which is intended to store the computer-implemented method described above, and can be read by a computer.

It is additionally possible for the individual components of at least one embodiment of the method or system described above (the load calculation agents, the load balancing service and the requirements module) to be embodied in a marketable unit and the remaining components in another marketable unit—as a distributed system so to speak.

BRIEF DESCRIPTION OF THE DRAWINGS

In the following detailed Figure-based description, non-restrictive example embodiments are addressed, together with their features and further advantages, wherein:

FIG. 1 shows a representational overview of an inventive system in accordance with an example embodiment, and FIG. 2 shows a flowchart in accordance with an example embodiment of the present invention.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments.

The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The underlying structure of an example embodiment of an inventive system for the load-balanced allocation of computer-aided medical task flows on at least one application server 100 of a server farm 10 is to be explained in conjunction with FIG. 1.

In day-to-day clinical operations, medical task flows as a rule comprise a large number of complex tasks, which must be performed in a certain chronological sequence. Here, the tasks can in turn encompass sub-tasks, and can be nested within one another or interleaved. The task "Examination planning for patient X", for example, may comprise the task "Produce an MR recording of the cranium". This task can for example encompass the sub-tasks "Generate measurement sequence for the MR scanner", "Record image data", "Post processing of recorded image data" etc.

Each task flow has specific request conditions. Thus, for example, the task flow "Generate MR brain scan" calls for different technical prerequisites from the task flow "Investigation of the blood for specific laboratory values". In the first case other technical parameters must be met, in order to enable execution of the task flow at all. In practice it is accordingly very important to be able to define and formulate the request conditions for medical engineering task flows too. According to the invention the request conditions can thus be configured in advance in a configuration phase. This generally takes place via a user interface, possibly in the form of a mask on the screen.

As shown in FIG. 1, administration of the clinical task flows takes place in a task flow administration system 300. The task flow administration system 300 is connected to the particular application server 100 via a network 200, and is likewise part of the server farm 10.

According to an embodiment of the invention, the servers 100 (in this document also referred to as application servers) are equipped with further modules, so that extended functionality can be performed on the servers 100.

In an example embodiment, each server 100 is equipped with a load calculation agent 102, which is intended to establish or calculate the load on the particular server 100. Basically a number of load calculation agents can be embodied on a server 100. This then makes sense, for example, if the load calculation represents a somewhat complex task, and calls for more computing power that can then be distributed among a number of load calculation agents. Alternatively it is also possible to provide a load calculation agent 102 for a group of servers 100, wherein the load calculation agent concerned 102 is to calculate the loads for the servers 100 assigned to it.

According to a further aspect of an embodiment of the present invention a server 100 can (but does not have to) comprise at least one program extension 101. It can also be the case—as also shown in FIG. 1—that individual servers 100 comprise either no program extension 101, just one program extension 101 or a number of different program extensions 101.

It is further envisaged that a load balancing service 104 is installed on at least one server 100 of the server farm 10 (in FIG. 1 on two application servers 100). It serves to receive the corresponding task flow from the task flow administration system 300 and to forward it, with or without further processing, to the particular load calculation agents 102 of the servers 100 of the server farm 10, in order that the load calculation agents 102 can then calculate their respective load and return it (to the load balancing service 104). Accordingly, the load balancing service 104 receives the results from the load calculation agents 102 and subjects them to further processing, in order to identify the target application server. Depending on the result of the method, one or more target application servers can be identified. A target application server is characterized by the fact that it is able to fulfill the recorded request conditions of the task flow according to the currently established load information for the identified server 100.

In conjunction with FIG. 2, a basic sequence is to be presented in accordance with an example embodiment of the present invention. As indicated in FIG. 2, the method can basically be divided into two consecutive phases. In a first configuration phase all parameters to be configured are configured. In a second load balancing phase the actual load that the task flow concerned requires is then established. The second load balancing phase has two further sub-phases, which can be executed independently of each other: These are a recording phase S10, S15, S20 for recording of parameters and a load calculation phase S25 during which the actual load calculation is performed.

In a first step S1, the request conditions are configured. Here it is possible to stipulate which request conditions are to be recorded.

In a second step S5 the load information to be recorded is configured.

The current task flow is recorded in a step S10, in that the task flow is to be started on the task flow administration system 300.

In a step S15, the request conditions for the task flow are recorded. The request conditions are first preferably sent to the load balancing service 104 by the task flow administration system 300.

The load information can subsequently be established in a step S20. This takes place via the load calculation agents 102. To this end each of the load calculation agents 102 passes on the request conditions recorded in each case to all load calculation agents 102. Each of the load calculation agents 102 then in turn passes these on to all hosted program extensions 101, which then in each case calculate a (part) result. The part-results from the program extensions 101 are subsequently consolidated by the associated load calculation agents 102 and sent to the load balancing service 104.

In a final step S25, the at least one target application server is calculated on the basis of the recorded request conditions and the recorded load information. The load balancing service 104 then likewise consolidates the results from the load calculation agents 102 and identifies the optimum application server 100. Thereafter, the load balancing service 104 returns the concrete result to the task flow administration system 300, so that this can then start the task flow on the identified target application server.

For the person skilled in the art it is obvious that it makes sense to display and make available the result of the load balancing procedure. Generally this takes place, for example, on the load balancing service 104, which has an appropriate user interface. It is likewise possible as an alternative also to forward the result of the method also to the task flow management system 300.

The request conditions are based both on physical system parameters and on logical features, and can in other developments relate to still further parameters of the system. By way of logical operators they can be formulated as a Boolean configuration in a variety of ways.

The load information which is to be recorded can likewise be configured. This preferably takes place via a correspondingly configured mask. To this end the program extension 101 is provided on a server 100. This preferably takes place in the form of a plug-in. The plug-in serves to accept calculation queries from the load calculation agent 102. A method "DetectFreeCapacity( )" is preferably called up for this purpose. A calculation query contains a complex feature condition (Server Query), as a rule with a plurality of request conditions. The program extension 101 now analyzes either all, some or none of the sub-conditions of the request condition, depending on the configuration. The analysis takes place using a standardized scale of 0-100. The value 0 here indicates that the corresponding feature of the request condition is fully utilized, and is no longer available to the current load query, while the value 100 is intended to signal complete availability. So to take the example of the volume rendering card with 8 GB of memory, a value of 25 means that 2 GB of the available 8 GB is still free. After all request conditions with their sub-conditions relevant to the program extension 101 have been analyzed accordingly, the program extension 101 returns an analyzed complex response to the load calculation agents 102.

In example developments of embodiments of the invention it is possible to subject this response to further processing. In particular it is possible to analyze the response with respect to the individual request conditions and/or the individual sub-conditions of a request condition. With the method "GetUtilisationInfo( )" the current load status of all sub-conditions is returned, based on the standardized scale of 0-100, while the method "GetStateInfo( )" contains any XML-based character string desired, which describes the internal status of the program extension 101. The character string can contain what is known as an XML style sheet, which serves to handle appropriate visualization of the information contained.

Further methods are additionally envisaged, in order to administer the internal status of the program extensions 101. These include the following methods: "HandleRequestAssigned( )", "HandleRequestNotAssigned( )", "HandleServiceStarted( )" and "HandleServiceFinished( )".

After a load calculation agent 102 has called up a method "DetectFreeCapacity( )" of a program extension 101, two further protocol steps follow. In a first step, the method "HandleRequestAssigned( )" or "HandleRequestNotAssigned( )" is called up. This takes place depending upon whether or not the server 100, on which the program extension 101 is running, is identified by the load balancing service 104 as the most suitable server, and thus as the target server for the task flow to be initiated.

Accordingly, program extensions 101 on a server 100 offer the possibility of effecting certain settings and configurations in advance. It is thus for example possible for the program extension 101 to mark reserved quotas for certain request conditions as occupied or release them again accordingly. As the second step a method "HandleServiceStarted( )" is called on all program extensions 101 running on the selected target application server. Calling up of the "HandleServiceFinished( )" method takes place in an analogous manner after the task flow has finished. These methods too serve to effect the acquisition or release of quotas of certain required request conditions.

A class "Clustermanagement" (which is assigned to the load balancing service 104) offers the method "GetServer( )" in order to identify the target application server for a specific request condition (ServerQuery).

A class "ApplicationServer" (which is assigned to the load calculation agent 102) offers the method "DetectFreeCapacity( )", in order to calculate the load for the dedicated server 100 in relation to the request conditions.

It can be seen that the particular advantage of the inventive solution lies in the fact that an embodiment of the inventive service for load-balanced allocation of task flows to a server farm 10 can be integrated into the existing task flow management system 300.

In addition it is not only possible to perform load balancing according to the algorithms known from the prior art (RoundRobin/LeastConnection), but also for specific medical and task flow-specific criteria to be configured. The target server 100 can for example be identified which is equipped for example with a volume rendering card or a high-performance graphics card for the particular application case. Heterogeneous server farms 100 can also be supported.

By way of an embodiment of the inventive configuration options of the request conditions it is possible not just to define conditions or sub-conditions in themselves, but also to stipulate how often the condition or sub-condition concerned must be fulfilled. The quantity of a request condition or of a sub-condition can thus also be recorded. It is also possible to prioritize the sub-conditions of a request condition in an appropriate manner through the allocation of weightings among them.

A program extension interface is preferably available on the respective load calculation agents 102 for installation of the program extension 101 on the servers 100. The program extension interface is in particular embodied in such a way that program code can be integrated which is, for example, based on .NET.

As already explained, a development of an embodiment of the invention aims to quantify the result of the load balancing process. Here, information is provided detailing which part of the task flow is to be passed to which target server 100 for processing. A result can, for example, be that 10% of task flow XY goes to server machine A, 20% to server machine B and 70% to server machine C.

In conclusion it should be pointed out that the description of an embodiment of the invention and the example embodiments are basically not to be seen as restrictive in respect of a particular physical realization of an embodiment of the invention. It is in particular evident to a relevant person skilled in the art that the invention can be realized partially or completely in distributed form in software and/or hardware and/or on a number of physical products—here in particular also including computer program products.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for identifying at least one target application server from application servers of a server farm to allocate computer-aided medical task flows, each of the application servers having a load calculation agent installed therein, the method comprising:
configuring, during a configuration phase, request conditions and load information of the application servers via a user interface of a load balancing service installed on at least one of the application servers, the request conditions indicating, via a plurality of linked logical operations, hardware required by an associated application server to perform the computer-aided medical task flow and the load information indicating what usage parameters are recordable by the associated application server; and
during a load balancing phase after the configuration phase,
recording the computer-aided medical task flow,
recording, at available application servers using the load calculation agent installed therein, the load information of a respective one of the available application servers by accumulating partial load information from different program extensions installed on the respective one of the available application servers, the program extension configured to,
analyze the request conditions required by the computer-aided medical task flow, and
return a complex response to the load calculation agent based on the analysis,
identifying, using the recorded load information and configurable load balancing criteria that prioritizes the application servers, at least one target application server from the application servers of the server farm that fulfills the request conditions of the recorded computer-aided medical task flow, and
outputting a load result list of the identified target application servers, the list quantifying the identified target application servers based on an extent to which the identified target application servers fulfill the request conditions configured during the configuration phase.

2. The method as claimed in claim 1, wherein at least one of the recording a computer-aided medical task flow, recording load information and the identifying is performed automatically.

3. The method as claimed in claim 1, further comprising automatically forwarding the task flow to the target application server for the purposes of execution.

4. The method as claimed in claim 1, wherein the request condition comprises a number of sub-conditions, and wherein the sub-conditions are linked with logical operators.

5. The method as claimed in claim 1, wherein the method is computer-implemented and is controlled in a software-based manner.

6. The method as claimed in claim 1, wherein the request condition comprises at least one of physical system parameters and logical features.

7. The method as claimed in claim 1, wherein the recording of the task flow is performed with configurable request conditions and the recording of the load information is executed in a configuration phase, which precedes a load balancing phase during which identification of the target application server is carried out.

8. The method as claimed in claim 1, wherein the recording of the load information is independent of the recording of the task flow.

9. The method as claimed in claim 1, wherein the load balancing service is installed on at least one application server of the server farm, the at least one load balancing service communicating with a task flow administration system and receiving the task flow from the task flow administration system, and the at least one load balancing service communicating with the load calculation agents of the application server and instructing the load calculation agents of the application server to calculate the load according to the currently configured criteria and collecting their result and subjecting the result to further processing where applicable.

10. A non-transitory computer readable medium comprising:
a computer program product with computer program code for performing, when the computer program code is executed on the computer the operation of identifying at least one target application server from application servers of a server farm to allocate computer-aided medical task flows, each of the application servers having a load calculation agent installed therein, the identifying including,
configuring, during a configuration phase, request conditions and load information of the application servers via a user interface of a load balancing service installed on at least one of the application servers, the request conditions indicating, via a plurality of linked logical operations, hardware required by an associated application server to perform the computer-aided medical task flow and the load information indicating what usage parameters are recordable by the associated application server; and
during a load balancing phase after the configuration phase,
recording the computer-aided medical task flow,
recording, at available application servers using the load calculation agent installed therein, the load information of a respective one of the available application servers of by accumulating partial load information from different program extensions installed on the respective one of the available application servers, the program extension configured to,
analyze the request conditions required by the computer-aided medical task flow, and
return a complex response to the load calculation agent based on the analysis,
identifying, using the recorded load information and configurable load balancing criteria that prioritizes the application servers, at least one target application server from the application servers of the server farm that fulfill the request conditions of the recorded computer-aided medical task flow, and
outputting a load result list which quantifies the identified target application servers based on an extent to which the identified target application servers fulfill the request conditions configured during the configuration phase.

11. A system for identifying at least one target application server from application servers of a server farm to allocate computer-aided medical task flows that require request conditions for execution, the request conditions being configurable, the system comprising:
at least one task flow administration system, to administer the computer-aided medical task flows by configuring, during a configuration phase, request conditions and load information of the application servers via a user interface of a load balancing service installed on at least one of the application servers, the request conditions indicating, via a plurality of linked logical operations, hardware required by an associated application server to perform the computer-aided medical task flow and the load information indicating what usage parameters are recordable by the associated application server;
load calculation agents installed on each of the application servers, the load calculation agents configured to,
calculate, during a load balancing phase after the configuration phase, a load on a respective one of the application servers on which the load calculation agent is installed by recording the load information of the respective one of the available application servers by accumulating partial load information from different program extensions installed on the respective one of the available application servers, the program extension configured to,
analyze the request conditions required by the computer-aided medical task flow, and
return a complex response to the load calculation agent based on the analysis, and
identify, using the load information and configurable load balancing criteria that prioritizes the application servers, at least one target application server from the application servers of the server farm that fulfill the request conditions of the recorded computer-aided medical task flow; and
at least one central load balancing service, installed on at least one of the application servers, to exchange data with the task flow administration system and with the load calculation agents, the load balancing service configured to output a load result list which quantifies the identified target application servers based on an extent to which the identified target application servers fulfill the request conditions configured during the configuration phase, wherein
the load balancing service includes at least one requirements module to record the request conditions for the computer-aided medical task flow, and
the load balancing service passes on the request conditions to the load calculation agents.

12. The method of claim 1, wherein the identification of the target application servers is performed automatically.

13. The system of claim 11, wherein the at least one task flow administration system is further configured to record the computer-aided medical task flows.

14. The method of claim 1, wherein the computer-aided medical task flow includes a sequence of at least two tasks.

15. The method of claim 14, wherein the at least two tasks are based on different software applications.

16. The method of claim 1, wherein the request conditions are configurable based on a medical problem corresponding to the task flow.

17. The system of claim 11, wherein the request conditions are configurable based on a medical problem corresponding to the task flow.

* * * * *